US 8,964,002 B2

(12) United States Patent
Ray et al.

(10) Patent No.: US 8,964,002 B2
(45) Date of Patent: Feb. 24, 2015

(54) METHOD AND APPARATUS FOR MAPPING IN STEREO IMAGING

(75) Inventors: Lawrence A. Ray, Rochester, NY (US); Richard A. Simon, Rochester, NY (US)

(73) Assignee: Carestream Health, Inc., Rochester, NY (US)

(*) Notice: Subject to any disclaimer, the term of this patent is extended or adjusted under 35 U.S.C. 154(b) by 480 days.

(21) Appl. No.: 13/178,537

(22) Filed: Jul. 8, 2011

(65) Prior Publication Data

US 2013/0010080 A1 Jan. 10, 2013

(51) Int. Cl.
| | | |
|---|---|---|
| *H04N 13/02* | (2006.01) | |
| *A61B 1/04* | (2006.01) | |
| *G01S 17/00* | (2006.01) | |
| *A61B 1/00* | (2006.01) | |
| *A61B 1/24* | (2006.01) | |
| *G01B 11/25* | (2006.01) | |

(52) U.S. Cl.
CPC . *A61B 1/04* (2013.01); *G01S 17/00* (2013.01); *A61B 1/00193* (2013.01); *A61B 1/24* (2013.01); *G01B 11/2527* (2013.01); *G01B 11/2545* (2013.01)
USPC .............. 348/47; 355/71; 356/3; 382/108; 382/154; 382/209; 348/46; 348/48

(58) Field of Classification Search
USPC ............ 355/71; 356/3.01; 382/108, 154, 209; 348/42–60
See application file for complete search history.

(56) References Cited

U.S. PATENT DOCUMENTS

| | | | |
|---|---|---|---|
| 6,754,370 B1 | 6/2004 | Hall-Holt et al. | |
| 6,937,348 B2 | 8/2005 | Geng | |
| 7,440,590 B1* | 10/2008 | Hassebrook et al. | 382/108 |
| 7,724,932 B2 | 5/2010 | Ernst et al. | |
| 2001/0048515 A1* | 12/2001 | Mei | 355/71 |
| 2003/0016366 A1 | 1/2003 | Takeda et al. | |
| 2007/0009150 A1* | 1/2007 | Suwa et al. | 382/154 |
| 2007/0046924 A1* | 3/2007 | Chang | 356/3.01 |
| 2009/0161966 A1* | 6/2009 | Lim | 382/209 |
| 2009/0221874 A1 | 9/2009 | Vinther et al. | |

OTHER PUBLICATIONS

Efrat, et al., "Curve Matching, Time Warping, and Light Fields: New Algorithms for Computing Similarity between Curves", J. Math. Imaging Vis., vol. 27, No. 3, pp. 203-216.
Glenn Hurlbert and Garth Isaak, "On the de Bruijn Torus Problem," Journal of Combinatorial Theory, Series A 64 (1): pp. 50-62.

(Continued)

*Primary Examiner* — Anner Holder
*Assistant Examiner* — Shanika Brumfield

(57) ABSTRACT

A method for registering a first imaging detector to a surface projects a sequence of k images toward the surface, wherein k≥4, wherein each of the k images has a pattern of lines that extend in a direction that is orthogonal to a movement direction. The pattern encodes an ordered sequence of labels, each label having k binary elements, such that, in the movement direction, any portion of the pattern that is k equal increments long encodes one label of the ordered sequence. The method obtains, for at least a first pixel in the first imaging detector, along at least one line that is parallel to the movement direction, a first sequence of k signal values indicative of the k binary elements of a first label from the ordered sequence of labels and correlates the at least the first pixel in the first imaging detector to the surface.

15 Claims, 8 Drawing Sheets

(56) References Cited

OTHER PUBLICATIONS

R. Malladi, J.A. Sethian, "Level Set and Fast Marching Methods in Image Processing and Computer Vision" Proceedings of IEEE International Conference on Image Processing, Lausanne, Switzerland, Sep. 16-19, 1996., 1996, pp. 489-492.

J.A. Sethian, Level Set Methods and Fast Marching Methods, Text Book, 2 pages Cambridge University Press, ISBN: 0 521 64557 3, 1996.

* cited by examiner

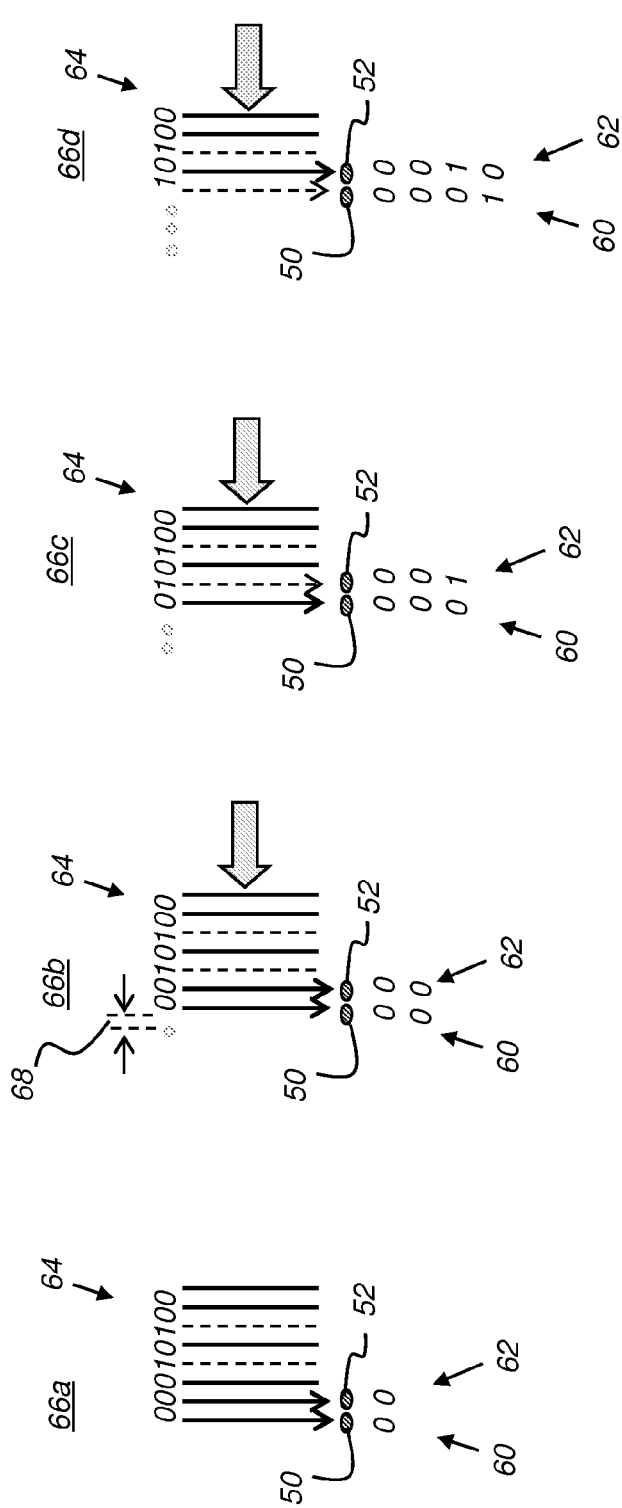

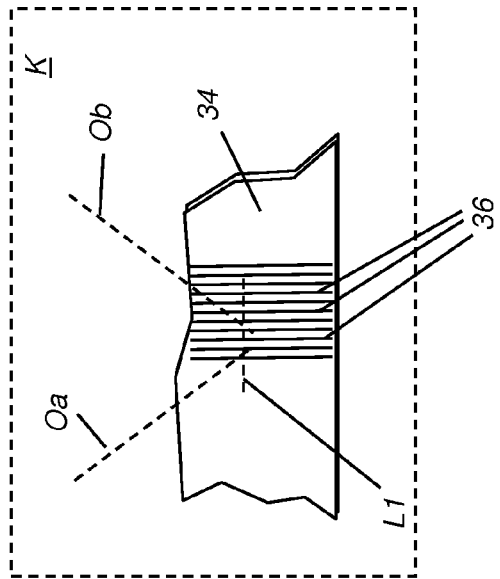
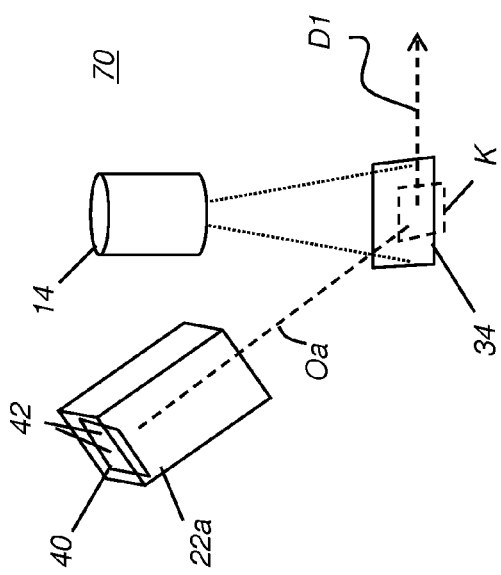
FIG. 8B
FIG. 8A

METHOD AND APPARATUS FOR MAPPING IN STEREO IMAGING

FIELD OF THE INVENTION

The invention relates generally to the field of surface imaging and more particularly relates to methods and apparatus for mapping surface locations to pixels in imaging of small objects or surfaces, such as in stereo imaging.

BACKGROUND OF THE INVENTION

The ability to determine the 3D structure of small objects is of value in a variety of applications, including intra-oral or dental imaging. Intra-oral imaging presents a number of challenges for detecting 3-D structure, such as those relating to difficulty in access and positioning, optical characteristics of teeth and other features within the mouth, and the need for precision measurement of irregular surfaces.

One common dental application for which surface imaging would be particularly advantageous relates to obtaining the profile of a tooth surface that has been prepared for the insertion of a dental crown. The typical method for fitting the crown is to take an impression of the prepared tooth and to forward the impression to a laboratory for fabrication. The returned crown then needs to be adjusted to make a proper fit. The process of making the impression is generally an unpleasant operation for the patient and too often yields unsatisfactory results.

An intra-oral surface image can be obtained using a single camera system that projects a light pattern, such as the barcode pattern described in U.S. Pat. No. 7,724,932 entitled "Three-dimensional modeling of the oral cavity" to Ernst et al. With such a system, however, contour over significant portions of the tooth surface can be difficult to image. Moreover, some external means must be provided in order to register reference points on the surface of the tooth with the image from the camera device.

Stereoscopic or stereo imaging has inherent advantages over single-camera imaging for detecting surface contour. A stereo intra-oral system comprises two cameras and a projector. The projector, typically positioned between the two cameras, illuminates the dental surface with a pattern in order to provide feature points as corresponding points for the stereo depth calculation. Enabling stereo imaging requires identifying the position of a point on an object in each image. This is often referred to as the correspondence problem. Solving the correspondence problem can be confounded by a host of reasons, including the lack of distinguishing features. One means of simplifying the problem is to illuminate the scene with structured light, i.e., light with a known pattern. The purpose of the patterned light is to overlay a number of features onto the object at fixed positions, so that these features can be used to register each camera and thus solve the correspondence problem. Various approaches and patterns can be used, such as to illuminate the object with lines of laser light or to illuminate the tooth surface or other area with different spectral content, such as using light patterns having different spectral content. One example of this approach is described in U.S. Pat. No. 6,937,348 entitled "Method and apparatus for generating structural pattern illumination" to Geng.

A correspondence problem that is common to solutions that use a projected light pattern relates to inherent localized dependencies. The region about a specific point of interest on a surface affects how well the corresponding pixel location for that point can be identified. Where the surrounding surface is sharply contoured or irregular, for example, there can be significant distortion that makes it difficult to provide accurate correspondence data.

Solutions using spectral patterning have also proved disappointing. Because of the nature of the tooth surface, for example, not all light wavelengths can be detected with equal accuracy. Thus, the multi-spectral approach described in the Geng '348 patent can be less satisfactory in some cases. Other patterning strategies encounter various problems related to signal detection due to the irregular contour of the tooth surface, the compact area over which imaging devices can be used, patient discomfort, and related factors that constrain the relative space that is available for imaging components, and other factors. Problems such as these continue to make it difficult to achieve the proper correspondence between two cameras as needed for stereo imaging.

Thus, although conventional methods for mapping points on a surface to imaging pixels have provided some measure of success, there is room for improvement. It would be highly advantageous to have a method for providing correspondence that is able to isolate a single pixel from its neighbors and accurately identify the corresponding surface point. There is, then, a need for apparatus and methods for providing improved correspondence mapping for single-camera and stereo imaging in the intra-oral environment and in other applications.

SUMMARY OF THE INVENTION

An object of the present invention is to advance the art of contour imaging, particularly for stereo imaging. Embodiments of the present invention may be of particular value for imaging small surfaces using stereoscopic or conventional single-camera imaging, including surfaces in confined spaces such as teeth or other intra-oral features. Advantageously, the present invention requires only monochrome light and provides a method for projecting a unique pattern to each of successive pixels along a line and providing a value indicative of measurement ambiguity.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for registering a first imaging detector to a surface, the method comprising: projecting a sequence of k images toward the surface, wherein k≥4, and wherein each of the k images comprises a pattern comprising a plurality of lines of light that extend in a direction that is orthogonal to a movement direction, wherein the transition from each one of the k images to the next image in the sequence is a spatial shift of the pattern by an equal increment along the movement direction, and wherein the pattern encodes an ordered sequence of labels, each label having k binary elements, such that, in the movement direction, any portion of the pattern that is k equal increments long encodes one label of the ordered sequence; obtaining, for at least a first pixel in the first imaging detector, along at least one line that is parallel to the movement direction, a first sequence of k signal values indicative of the k binary elements of a first label from the ordered sequence of labels; and correlating the at least the first pixel in the first imaging detector to the surface.

According to an alternate aspect of the invention, there is provided a method for registering first and second imaging detectors to a surface, the method comprising: projecting a sequence of k images toward the surface, wherein k≥4, and wherein each of the k images comprises a pattern comprising a plurality of lines of light that extend in a direction that is orthogonal to a movement direction, wherein the transition from each one of the k images to the next image in the sequence is a spatial shift of the pattern by an equal increment along the movement direction, and wherein the pattern encodes an ordered sequence of labels, each label having k binary elements, such that, in the movement direction, any portion of the pattern that is k equal increments long encodes one label of the ordered sequence; obtaining, for at least a first pixel in the first imaging detector and at least a second pixel in the second imaging detector, along at least one line that is parallel to the movement direction, a first sequence of k signal values indicative of the k binary elements of a first label from the ordered sequence of labels; and correlating the first and second imaging detectors to each other according to the obtained first sequence of k signal values.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 5A-5D show a sequence used for image projection and detection that labels pixels along a line.

FIGS. 8A and 8B show features of a pattern projection and detection system used in a single-camera embodiment of the present invention.

DETAILED DESCRIPTION OF THE INVENTION

Figure 1:
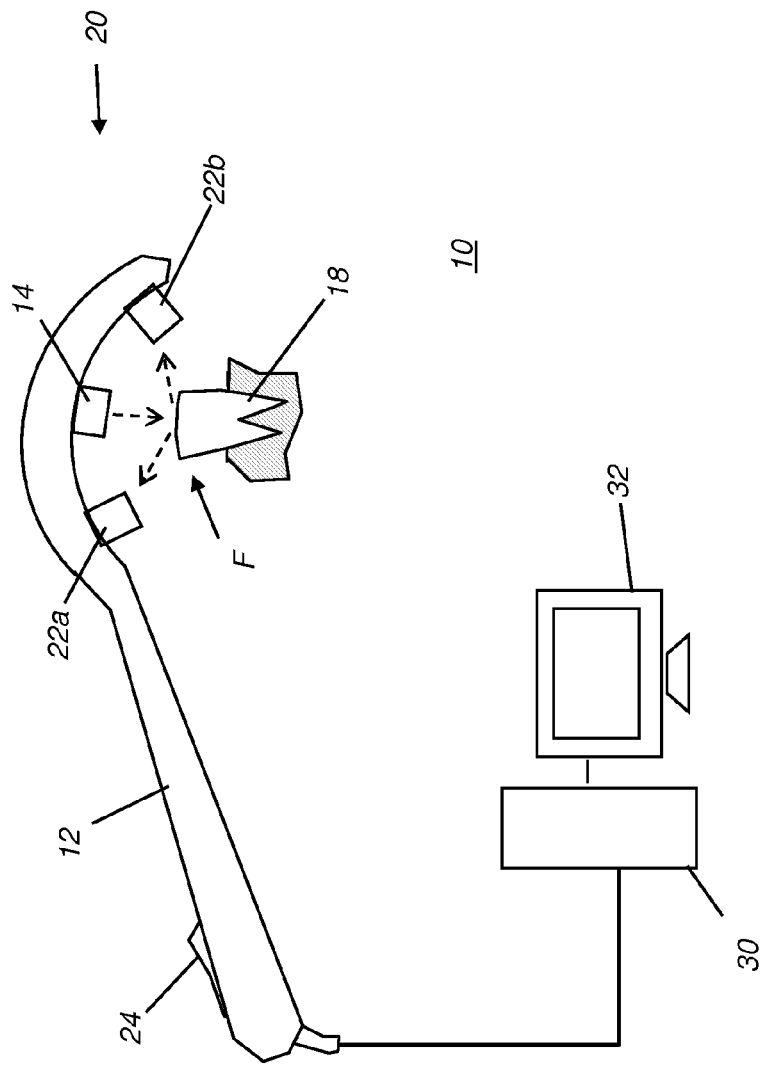
FIG. 1 shows components of a stereo intraoral imaging apparatus according to an embodiment of the present invention.

The following is a detailed description of the preferred embodiments of the invention, reference being made to the drawings in which the same reference numerals identify the same elements of structure in each of the several figures.

Where they are used, the terms "first", "second", and so on, do not necessarily denote any ordinal or priority relation or position relative to the beginning of an ordered sequence, but may simply be used to more clearly distinguish one element from another.

Embodiments of the present invention address difficulties in identifying points along the contour of intricate surfaces, such as those of the tooth. Due to topographic variations, the projected signal on a dental surface is often transformed, such as by being stretched in some regions and compressed in others. The inventors have observed that this situation is not unique to dental topography, but also occurs in speech recognition and a myriad of other applications. One approach to address this problem is commonly referred to as a dynamic time-warping algorithm (DTW). Dynamic time-warping examples and approaches are discussed, for example by A. Efrat, et. al., in an article entitled "Curve Matching, Time Warping, and Light Fields: New Algorithms for Computing Similarity between Curves", *J. Math. Imaging Vis.*, vol 27, No. 3, pp. 203-216. Although the present invention is not directly related to curve-matching or other data warping applications, embodiments of the present invention adapt aspects of some DTW approaches to recover encoded information projected onto the dental surface.

FIG. 1 is a schematic diagram that shows components of an imaging apparatus 10 for stereo dental imaging according to an embodiment of the present invention. A stereo image acquisition unit 20 has two cameras as imaging detectors 22a and 22b and a projector 14 within a handle 12 for imaging a tooth 18 or other object in an imaging field F. A switch 24 is provided in handle 12 for initializing image capture. Projector 14 projects a sequence of images, formed and arranged as described subsequently, as instructed by a host processor 30. Host processor 30 may be any of a number of types of computer, workstation, or dedicated microprocessor or programmed logic device that executes stored instructions and includes logic processing and memory circuitry. Host processor 30 may be a separate component, as shown in FIG. 1, or may be wholly or partially integrated into handle 12. Host processor 30 obtains and processes images captured by imaging detectors 22a and 22b. A display 32, in signal communication with host processor 30, provides a mechanism for display of acquired images from imaging apparatus 10. An optional set of filters is provided for improving image quality, such as by reducing specular reflection, for example.

Figure 2:
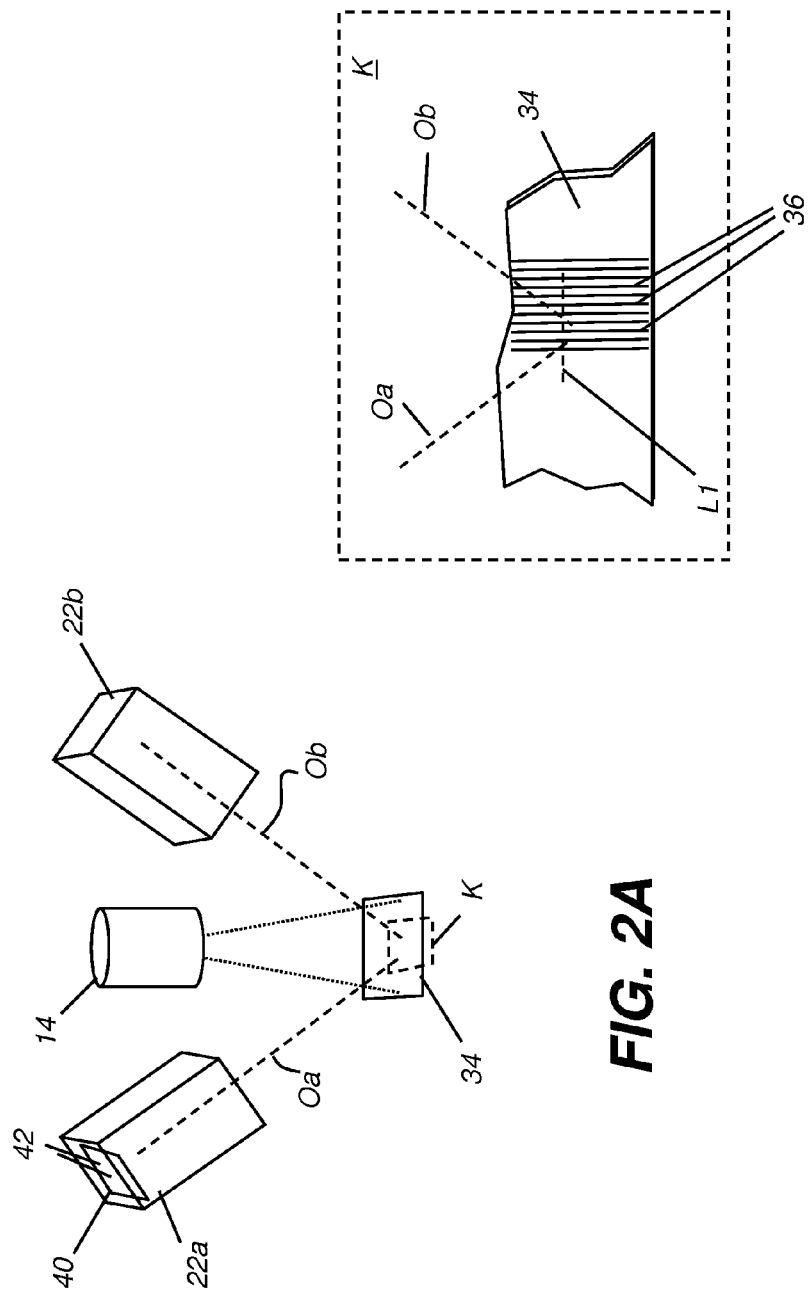
FIGS. 2A and 2B show features of pattern projection and detection used in an embodiment of the present invention.

FIGS. 2A and 2B show aspects of the geometry of stereo imaging apparatus 10 for imaging a surface 34, applicable to embodiments of the present invention. Imaging detector 22a has a corresponding optical axis Oa; imaging detector 22b has a corresponding optical axis Ob. As shown at imaging detector 22a, each imaging detector has an internal sensor array 40 with multiple pixels 42 that correspond to "pixel" locations with respect to surface 34. Embodiments of the present invention enable each pixel 42 of imaging detectors 22a and 22b to be identified with, or correlated to, a corresponding area on surface 34 that is imaged as a single pixel, often termed a "pixel-diameter" location. As shown in an inset K, projector 14 projects lines of light 36 onto surface 34, wherein the projected lines of light 36 extend in a direction that is orthogonal to a line L1 connecting axes Oa and Ob from the cameras, imaging detectors 22a and 22b. The distance between lines of light 36 at the imaging field preferably is in increments that correspond to one pixel width, or an integer multiple of one pixel width, at imaging detectors 22a and 22b.

The surface of the human tooth has challenging optical properties for contour imaging. When illuminated, dental enamel tends to scatter light, so that artificial textures blur, making precise measurements difficult. This effect can be noted for light throughout the visible spectrum, but is least noticeable for light at blue wavelengths (approximately 425-470 nm). Because of this, embodiments of the present invention project and detect a pattern of monochrome light in the blue spectrum.

Regardless of the spectral composition of the light source, if a pattern is projected, there will be some points on the tooth surface that have illumination and other points with little or no perceptible illumination. Due to internal scattering, the level of illumination can be difficult to accurately determine for points on the surface. As a result, it is advantageous to form and detect light patterns with binary illumination levels.

Structured Light Patterns

A number of imaging solutions are known that use a pattern of projected lines of light directed onto a surface for contour measurement. However, as is noted in the background material, conventional solutions that use structured light fall short of what is needed for establishing accurate correspondence between the two imaging detectors used in stereo imaging applications. Embodiments of the present invention address this problem by projecting a sequence of patterns that enable pixels along line L1, or along lines parallel to L1, to have specific label assignments. To do this, embodiments of the present invention utilize a class of structured light patterns that provide patterns in an ordered sequence of elements. This sequence is in the spirit of Hamilton or de Bruijn patterns, with modifications to help provide more readily identifiable signal content. The following is a brief description of the de Bruijn or Hamilton sequence and how these can be used to generate a series of linear or area patterns.

Consider a set of k symbols. It is well known that for a number system of base k, a set of $k^n$ numbers can be represented with n elements chosen from the k symbols. For example, if k=10 and n=3, then the set of $10^3$ numbers consists of the numbers from 0 to 999.

Given a linear array of n elements, a circular array is formed by addressing the elements of the linear array using an index with modulo n arithmetic. Thus, the elements are indexed from 0 to n−1 and the mth element refers to the m mod(n) element of the linear array. Three consecutive elements of the array beginning at n−1 are indexed as n−1, 0, and 1. A similar idea can be applied to higher dimensions, and for two dimensions the result is referred to as a toroidal array.

An illustrative example is the array of binary characters:

$$00000100011001010011101011011111 \quad (1)$$

This array has length 32 and is one period of a repeating pattern. One property of this pattern of particular interest is that any 5 element contiguous sub-string is unique. The pattern wraps in circular fashion. Since there are only 32 unique binary patterns of length 5, there is a one-to-one mapping of this array to the integers 0-31.

The pattern in the array shown at (1) also has the property that unique, successive 5-element substring values can each be formed by a simple shift of one character. If one considers each substring in the sequence as a label, then each position of the array, that is, each 5 element contiguous sub-string, provides a unique label. Stated differently, where k=5, the characters or elements in any portion of the pattern that is 5 equal character-increments long encodes one label of the ordered sequence. This pattern is a type of de Bruijn cycle.

A $(k^r, k^s; m, n)$ de Bruijn torus is a k-ary $k^r \times k^s$ toroidal array with the property that every k-ary m-by-n array occurs exactly once contiguously on the torus. The selection of r, s, m and n is not arbitrary and there are conditions that need to be met for a de Bruijn torus to exist. These conditions are described, for example in an article by Glenn Hurlbert and Garth Isaak, "On the de Bruijn Torus Problem," *Journal of Combinatorial Theory, Series A* 64 (1): 50-62). The property that every m×n array occurs exactly once implies there is a one-to-one and onto mapping from the set of m×n arrays to the double index set (i, j) wherein i is an element of the set of $k^r$ numbers and j is an element of the set of $k^s$ numbers. As a result knowledge of an m×n array provides sufficient information to determine a position within the array.

Most often the set of symbols is a two-element set, such as {0,1}, though the method is not limited to a binary set. There is a well-known mapping of a torus to a rectangle by assigning the right edge of the rectangle to the left edge, and the top of the rectangle to the bottom of the rectangle. The inventors have applied this thinking to the correspondence problem by illuminating an object with such a pattern and imaging the object with a pair of stereo cameras to generate a large number of identifiable feature points that are readily matched. In another embodiment, a single camera could alternately be used, as described in more detail subsequently.

In considering linear patterns, an alternative method of describing the de Bruijn pattern sequence is to consider the labels as nodes on a graph, with a node being connected to other nodes that are formed by removing the first (left-most) element of the label, shifting each of the remaining elements one increment left, and adding one of the symbols on the right. For instance a node with the label 10011 is connected to nodes 00110 (shifted left and 0 added) and 00111 (shifted left and 1 added). For a full binary de Bruijn cycle of length $2^n$, there are $2^n$ nodes and each node has two connections to other nodes. The result is a directed graph. In this characterization, the de Bruijn cycle is a circuit in the graph that visits every node precisely once, a so-called Hamiltonian or Hamilton cycle or circuit. The de Bruijn pattern is a Hamilton circuit of all $k^n$ combinations, wherein k is the number of states and n is the length of the sub-string.

As noted earlier, embodiments of the present invention adapt the de Bruijn pattern to address the problem of correlating a pixel in an image sensor to a point location, such as a point on the surface of the tooth. However, it can be observed that the de Bruijn pattern itself includes a number of nodes or labels that can be difficult to detect as a signal, such as 00000 or 11111, for example, in which there are no transitions between binary elements in the label. For the purpose of improved signal detection, an embodiment of the present invention modifies the de Bruijn pattern, using a de Bruijn subcycle that uses a proper subset of all of the possible $k^n$ labels to reduce the number of possible nodes or n-character combinations. In the de Bruijn subcycle that is used, there is a change in binary state at least once for each sub-string, i.e., each sub-string has at least one 1 and one 0, for example. Following this practice helps to improve the dynamic range of the signal received at a pixel and to enable methods for more accurate identification of the intended label. When using this type of sequence, sub-strings not meeting these criteria can be considered as forbidden strings. This can be generalized to sub-strings of length n, for some desired length, and the minimum number of times each state needs to be activated within a sub-string can determine the set of acceptable sub-strings and its complement, the set of forbidden strings.

As another example, consider sub-strings of length 6. The number of possible strings or labels of length six, is $2^6$=64. However, when restricted to labels that have at least two 1 elements and two 0 elements, there are only 50 labels meeting this criteria, computed as follows:

$$\binom{6}{2} + \binom{6}{3} + \binom{6}{4} = 50 \quad (2)$$

Such a pattern is given by:

$$01100001111001110001100100110110100101010001011101 \quad (3)$$

As noted previously, the 6-element sub-strings can be considered as nodes of a graph, and the Hamilton circuit as a path the visits each node precisely once per cycle and moreover returns to the first node after visiting the $50^{th}$ node. It can be observed that this type of repeating sequence is advantageous because it allows an additional way to evaluate whether or not a detected label is likely at a particular location.

Figure 3:
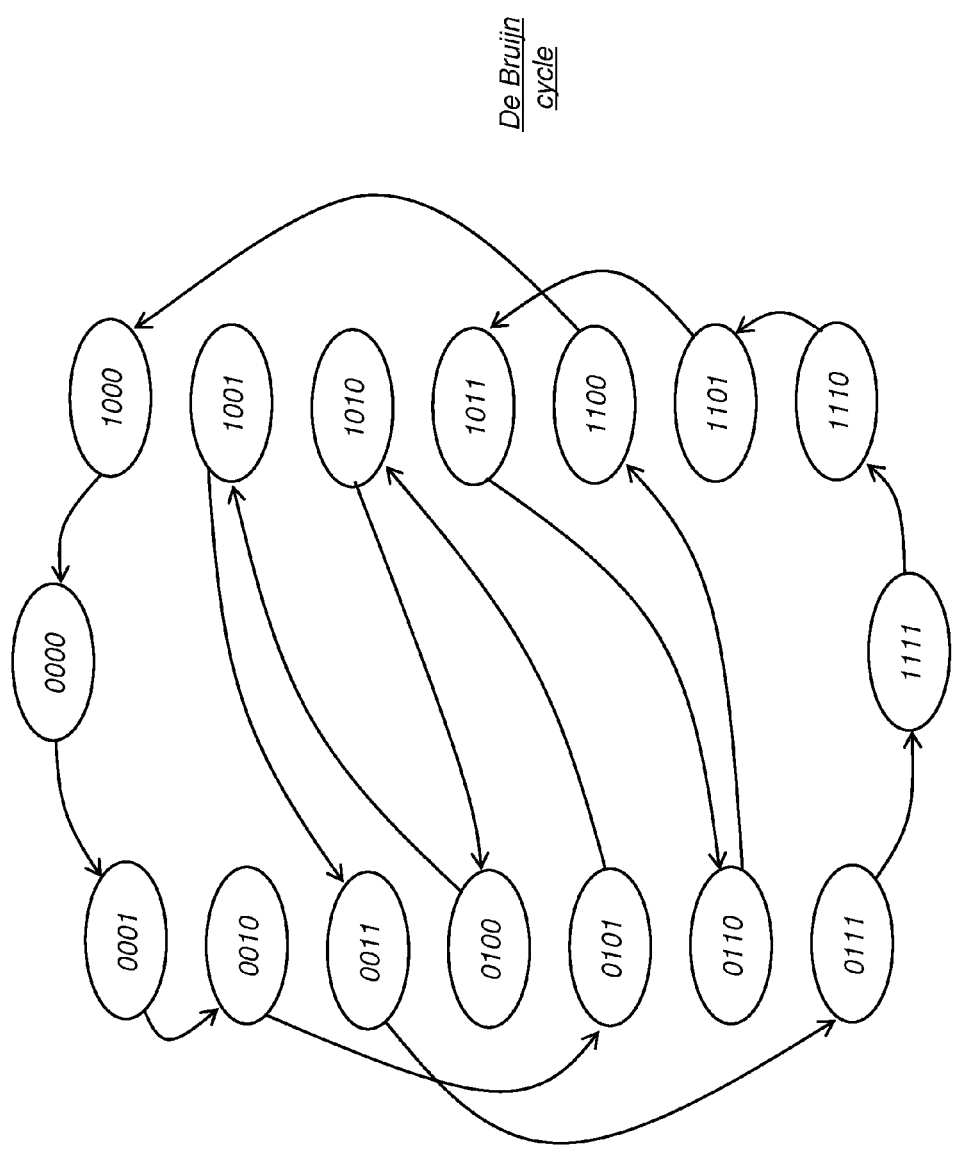
FIG. 3 is a graph showing an exemplary Hamilton circuit.

As a simple example, FIG. 3 shows the Hamilton circuit for a 4-element de Bruijn cycle of length $2^4$=16. Each of the sixteen 4-element combinations can be considered as a character or label. As noted previously, for signal detection accuracy, it is convenient to eliminate 0000 and 1111 from this circuit, forming a subset of the complete de Bruijn cycle, that is, a de Bruijn sub-cycle, so that each node has at least one transition (a 0-to-1 transition or a 1-to-0 transition). This yields the Hamilton circuit of FIG. 4. Again, every substring, of length 4 (n=4) is unique and forms a node in the graph shown. The following pattern can be used to generate each 4-element node of the graph of FIG. 4, in sequence (again, wrapping around to the beginning as needed):

$$00010100111011 \tag{4}$$

Figure 4:
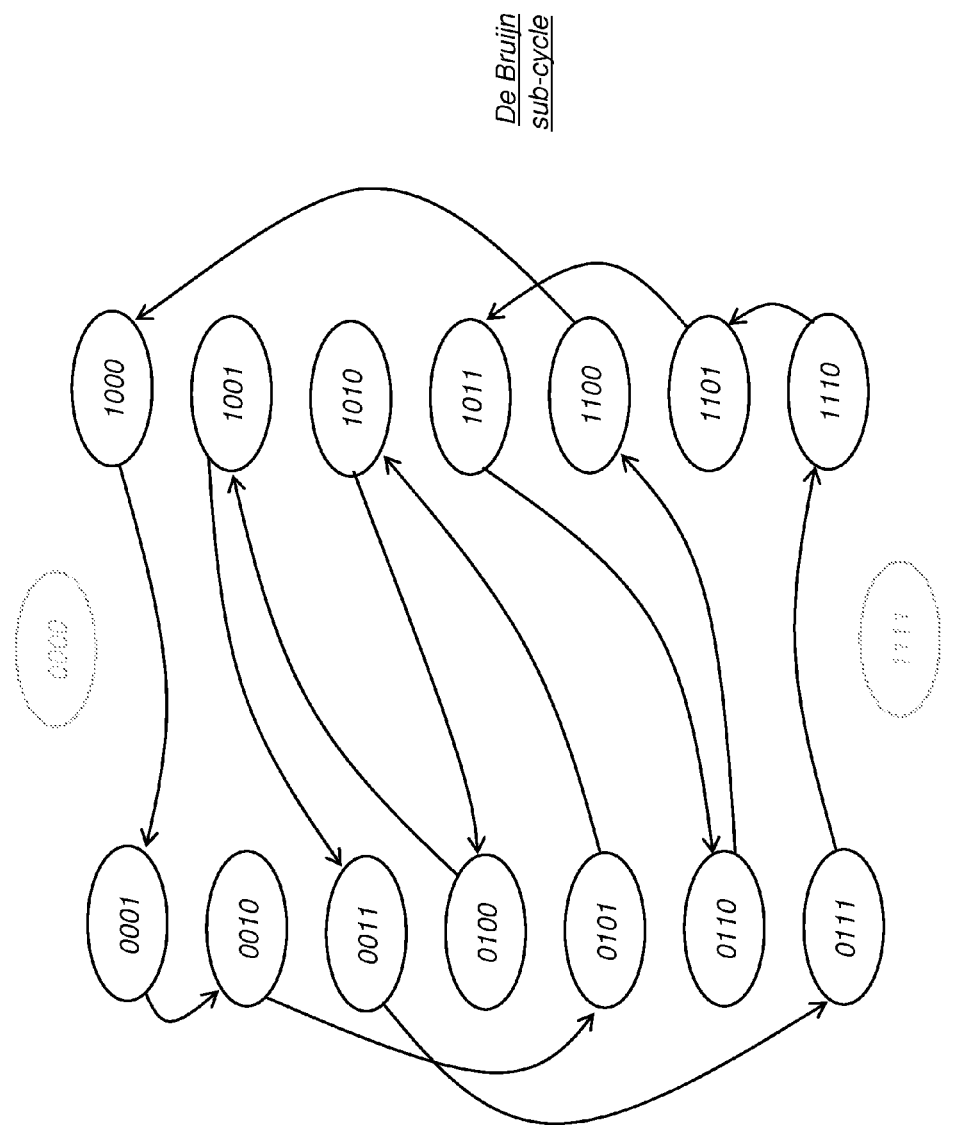
FIG. 4 is a graph showing an exemplary Hamilton circuit with values 0000 and 1111 removed.

Beginning from any consecutive 4 element substring or character or label in pattern (4), the transition to the next substring or label, as arranged in FIG. 4, is achieved by shifting by an increment of one element, so that the left-most element drops off and the next 1 or 0 in the sequence is appended in the right-most position of the substring. Beginning at the far left of the string, for example, the complete sub-cycle can be followed as expressed in this abbreviated sequence:

$$0001 \rightarrow 0010 \rightarrow 0101 \rightarrow 1010 \rightarrow \ldots \rightarrow 1000 \rightarrow 0001$$

This same progression can be traced from node to node in FIG. 4.

In a Hamilton circuit as shown in FIGS. 3 and 4, each node has degree 2, that is, each node has 2 connections: one connection from a previous node and one connection to a next node. By moving from node to node, it can be seen that a unique sequence is formed and that each node is visited once per cycle. The inventors have found that, using the encoding of the nodes as labels, the de Bruijn and Hamiltonian sequencing described hereinabove can thus be used to generate a repeating sequence of labels that can be provided by a sequencing operation, yet are clearly distinguishable from each other. Embodiments of the present invention utilize this capability to help prevent ambiguity in correlating spatial locations to pixels and to address the correspondence problem for stereoscopic imaging.

While application of the de Bruijn sub-cycle sequence has some advantages, however, significant practical problems prevent these encodings from being used directly. As has been noted earlier, the topography of the tooth or other object can distort projected patterns making the decoding process difficult. An area needs to be identified and points near object edges may not have sufficient area to illuminate a required sub-array. The tooth or other object may be colored in such a way that confounds the information in the sub-array. Apparatus and methods of the present invention address these difficulties to use de Bruijn patterns more effectively for providing correspondence information.

Assigning a Label to Each Pixel

In the apparatus shown in FIGS. 1 and 2A, each pixel in imaging detectors 22a and 22b corresponds to a point on the surface 34 that is being imaged. Correspondence of the cameras or other type of imaging detectors is obtained by correlation, identifying the pixel in each imaging detector that senses light from the same known point on the surface. Lines of light from projector 14 are used to provide patterns that uniquely differentiate one pixel from its neighbors. This is done by assigning a unique label to the pixel, in the manner described in the example sequence of FIGS. 5A-5D. Two adjacent pixels 50 and 52 are shown at successive times. A light pattern 64 is directed to the surface four times, shifted toward the left by one pixel each time. An image is captured each time, so that each pixel receives four values from light pattern 64. In this example, light pattern 64 is a series of lines of light that encode a portion of the pattern shown in (4) above and described with reference to the graph of FIG. 4.

With light pattern 64 directed at a first position 66a in FIG. 5A, a first line of light encodes a 0 which is detected at pixel 50 and stored in a line stack 60 for that pixel. Similarly, a second line of light encodes a 0 which is detected at pixel 52 and stored in a line stack 62 corresponding to that pixel. With light pattern 64 directed at a next position 66b, pattern 64 is shifted left from the projector by a one-pixel increment 68. Again, each pixel 50, 52 receives a line of light that encodes a 0 and a corresponding 0 is stored in each line stack 60 and 62. At a next position 66c, pattern 64 is again shifted by the projector, to the left by a one-pixel increment 68. Pixel 50 records a 0 and pixel 52 now records a 1. With light pattern 64 directed at a fourth position 66d, pattern 64 is again shifted left by a one-pixel increment 68. Pixel 50 now records a 1 and pixel 52 records a 0. At the conclusion of this 4-image sequence, line stack 60 stores a label 0001 for pixel 50. Line stack 62 stores a label 0010 for adjacent pixel 52. It can be seen that by extending this pattern to subsequent and prior pixels along a line of pixels, each pixel in the line can be assigned a value, that is, a four-element label, that distinguishes it from its neighboring or adjacent pixels. As noted earlier, this pattern is cyclical and thus repeats; however, there is enough differentiability in the light delivery and detection scheme to correlate pixels detected along the same line by each imaging detector 22a and 22b using this arrangement.

The simplified sequence in FIGS. 5A-5D, using short labels of length 4, shows the principle by which a de Bruijn sub-cycle can be used to encode an ordered sequence of labels, one to each pixel along a line that extends across a surface to be profiled. In practice, this arrangement is most efficient when lines of light that encode the de Bruijn sub-cycle sequence are separated from each other so that increment 68 is one pixel wide. Alternate distances could be used, but would require more complex processing. Labels of longer lengths are advantaged; each element of the label requires one image projection and capture operation. While four images can be used to encode labels using the graph sequence shown in FIG. 4, the use of additional images provides even better differentiability between pixels, allowing labels of 5-, 6-, 7-, 8-characters or more in length. Labels formed using binary (1,0) characters are advantaged for ease of detectability; however, intermediate light levels between fully on and fully off could be used to enhance the code depth available for each label, provided that detection works well enough to distinguish one level of light from another.

Data Structures and Processing

Methods for assigning an encoded label to each pixel and for processing the label assignments can be executed in any of a number of ways. One algorithm used to assign labels along each scan line of the image employs various elements and approaches adapted from dynamic time-warping (DTW) and the so-called fast marching algorithm (described in the textbook by J. A. Sethian, entitled *Level Set Methods and Fast Marching Methods*, Cambridge University Press, 2005).

Pixel Cost (LCost)

A feature of the algorithm in embodiments of the present invention is the definition of cost related to the choice of a label. The cost metric has two basic components: one relates to measured signal ambiguity for each data element in a label, assigning a low value to a measured signal that is unambiguous, indicating that the signal is clearly 1 or 0, for example; the other component relates to the label itself and its position in the sequence of labels according to the pixel sequence, so that a low value indicates that the detected label for a pixel has the expected relation to the detected label for the pixel preceding and the pixel following.

For the example that follows, a label ($b_1b_2b_3b_4b_5b_6$) has six binary elements, with at least two 0's and at least two 1's. Consider a column from the line stack for a 6-character label, which has six values, ($p_1$, $p_2$, $p_3$, $p_4$, $p_5$, $p_6$). One potential measure of the choice of label is a pixel cost μ or LCost that can be computed as follows:

$$\mu = \sum_{i=1}^{6} \begin{cases} \frac{M-p_i}{M-m} & \text{if } b_i = 1 \\ \frac{p_i-m}{M-m} & \text{if } b_i = 0 \end{cases} \text{ where } \begin{cases} M = \max_i p_i \\ M = \min_i p_i \end{cases} \quad (5)$$

For each individual binary element, the cost is between 0 and 1, depending on the signal obtained. The resulting pixel cost for the 6-character label, then, is a value between 0 and 6 and indicates a level of confidence in the measured data.

A special case occurs in (5), when M=m, indicating that the binary value is non-ambiguous. For this case, we assign the lowest possible pixel cost, μ=0. When the pixel cost value is 0, all brightly illuminated pixels have the same high value and all dimly illuminated pixels similarly have the same low value. In practice, the pixel cost μ can be higher due to factors such as noise, border effects, or partial volume effects, for example.

Label Cost (TCost)

Another component of processing relates to the label ordering sequence. As noted with respect to FIGS. 4 and 5A-5D, the projected pattern encodes the labels in a specific order. Where the detected ordering is as expected, that is, matches the ordering encoded in the projected signal, the label cost is low; deviation from the expected ordering indicates a problem and has a correspondingly higher cost.

The most likely situation is that neighboring labels will remain the same or increase by one relative to the mapping that is used. A simple metric for the label transition τ is as follows:

$$\tau(l_1,l_2)=\kappa(l_2-l_1) \bmod 50 \quad (6)$$

wherein κ is a scalar, nominally set to 0.02 and $l_1$ and $l_2$ are labels relative to the mapping. Thus, sequential labels have a small measure and the measure increases as the span between labels increases. The value τ is referred to as the transition cost or TCost.

The overall measure of an entry of the line stack from the label assigned to the neighboring entry of the line stack is the sum of μ and τ. This is referred to as the total cost.

For one algorithm using this cost strategy, the sequence starts on one side of the scan line and assigns labels to successive pixels along the scan line in order to determine the assignment that produces the minimal cost.

Data Structures

Figure 6A:
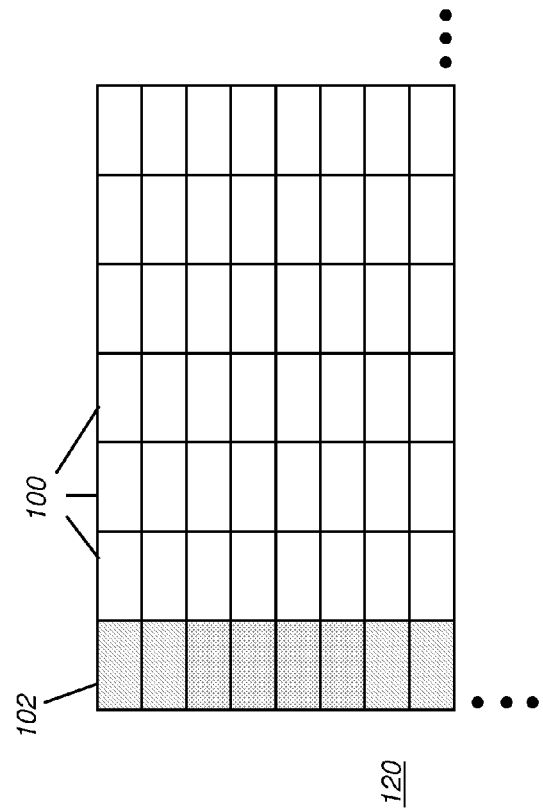
FIGS. 6A-6C show data structures used in an embodiment of the present invention.
Figure 6B:
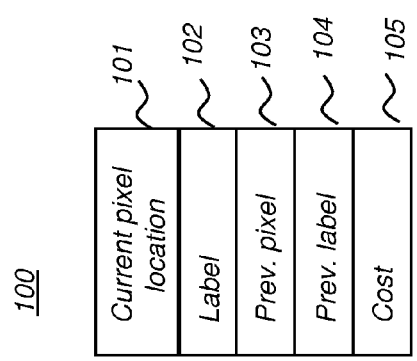
Figure 6C:
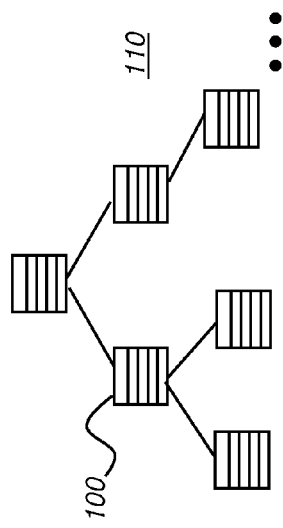

Using the labeling approach just described, FIGS. 6A-6C show a number of data structures used for undertaking the labeling problem according to an embodiment of the present invention. A basic data packet 100 consists of a current pixel location in the line 101, a current label 102, a previous pixel location 103, a previous label 104, and a cumulative cost 105. Another auxiliary data structure is the well known heap sort using a heap 110. Basic data packets 100 that are generated are placed on and removed from heap 110 based upon the minimal cost entry 105 of the basic data packets in the heap. The final data structure is referred to as a skein 120, that consists of an array of basic data packets 100. Skein 120 has a row for each label, and one initial column plus other columns, one for each pixel along a line.

Figure 7:
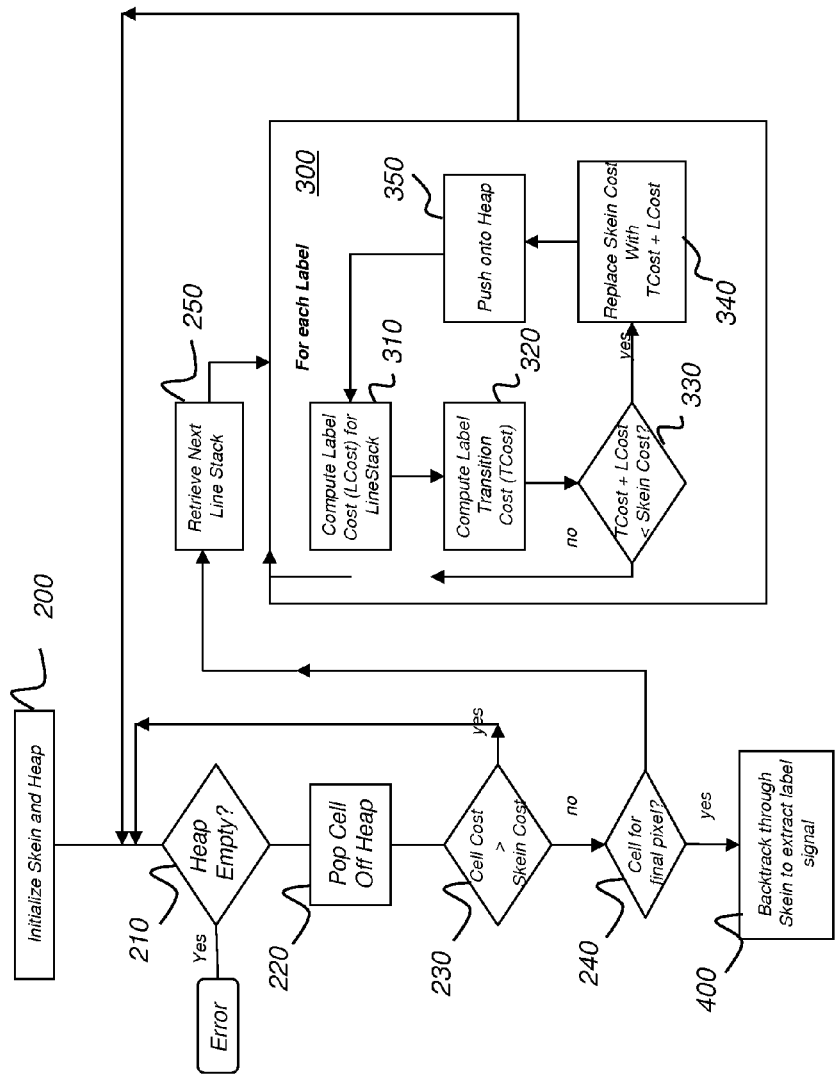
FIG. 7 is a logic flow diagram that shows pixel processing for stereo imaging according to an embodiment of the present invention.

Logic flow of the algorithm is shown in FIG. 7. An initialization step 200 initializes the skein 120 and the heap 110. This is done by creating a basic data packet for each label with the current pixel location as zero, the previous pixel location as −1, the previous label as −1, the current label, and the cumulative cost as zero. The basic data packets are placed in the initial column of skein 120 and each is added to heap 110. A step 210 is a check to determine if the heap is empty. This should not happen, and if this occurs an error condition is returned. Heap 110 is sorted with the least costly cumulative cost basic data packet 100 on top. This packet 100 is removed from the heap at step 220. At a comparison step 230 the cumulative cost contained in this basic data packet 100 is compared to the cumulative data cost in the skein 120 array at the current label and the current pixel location of the skein. If the cost exceeds the cost in the skein, then the basic data packet is discarded and the process returns to step 210. The next comparison in a comparison step 240 is to check to determine if the basic data packet has the current pixel location being the end of the scan line. If this condition occurs then a signal is extracted by a backtracking process described below, backtracking step 400.

Continuing with the steps in FIG. 7, at a step 250 the line stack 60 for the next pixel location, the pixel location one greater than the current pixel location, is retrieved. Next a set of steps 300 execute for each label. A cost computation step 310 computes the cost for the label and the line stack. A label transition cost computation step 320 computes the cost to transition from the current label of the basic data packet extracted from the heap to the current label. A comparison step 330 adds these two costs to the cumulative cost 105 in the basic data packet extracted from the heap and compares the cost to the costs in the skein 120 at the next pixel location and the label. If the cost is greater than the cost contained therein, the process moves to the next label; otherwise, skein 120 is updated in an update step 340 with the current cost. The appropriate basic data packet is added to the heap in a push step 350. The algorithm terminates once a basic data packet 100 is removed from the heap that contains the last pixel in the line. The skein contains backward pointers to the transition that led to the current data packet. The basic data packets in the skein also contain the label. The labels signal is then formed in backtracking step 400 by moving from the last pixel to the first pixel by the backward pointers. This process cycles one or more times, depending on the length of the pattern.

The sequence described with respect to FIG. 7 can be repeated for each of any number of lines or rows of pixels received from imaging detectors 22a and 22b. Given the data acquired using the sequence shown, conventional image processing techniques can be used to correlate and register pixels received by imaging detector 22a with corresponding pixels received by imaging detector 22b.

Referring again to FIG. 1, the function of host processor 30 is to execute the logic for controlling the pattern projected from projector 14 and processing the image data obtained from both imaging detectors 22a and 22b, including the correspondence mapping described hereinabove. It should be emphasized that the data structures and algorithms described herein are exemplary and show an embodiment of the present invention. However, other arrangements of data and process sequencing are possible using the basic sequence of embodiments of the present invention. In an alternate embodiment, the function of host processor 30 can be distributed, shared between multiple processors, including networked processors, for example, to obtain similar results. Host processor 30 may provide operator selection of variables related to the pattern type, including number of binary characters used to form labels for obtaining correspondence between the imaging detectors.

Embodiments of the present invention can be used in a stereoscopic imaging apparatus as well as for correlating points on a surface with pixels in a single-camera imaging apparatus. Referring to FIGS. 8A and 8B, for example, a portion of an image acquisition unit 70 having only one imaging detector 22*a* is shown. The sequence of images of lines from projector 14 moves in a single direction D1, with the projected lines extending orthogonally with respect to direction D1.

Projector 14 itself can be any of a number of types of projector apparatus, including a scanning laser device, a picoprojector, or other apparatus capable of projecting a light of sufficient resolution. In an embodiment of the present invention described with reference to FIGS. 5A-5D, projector 14 is capable of projecting lines at near-pixel width or sub-pixel width resolution. Laser-based projectors can be particularly advantaged for this function.

It can be appreciated that the methods of the present invention adapt dynamic time-warping techniques to address particular problems in contour imaging for small objects. By generating and projecting a signal pattern that labels, in an ordered manner, successive pixels spaced at equal distances from each other, embodiments of the present invention enable detection of points on an irregular surface, including cases where an irregular contour tends to distort or warp the projected pattern. The particular cost computation techniques used to correlate labels to pixels described herein are one example of a mapping method. It can be appreciated that any of a number of alternate methods can be used to provide this mapping.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for registering a first imaging detector to a surface, the method comprising:
projecting a sequence of k images toward the surface, wherein k≥4, and wherein each of the k images comprises a pattern comprising a plurality of lines of light that extend in a direction that is orthogonal to a movement direction, wherein the transition from each one of the k images to the next image in the sequence is achieved by a spatial shift of the pattern by an equal increment along the movement direction so that the leftmost image is removed and the next image in the sequence is appended as a right-most image in the pattern, and wherein the pattern encodes an ordered sequence of labels, each label having k binary elements, such that, in the movement direction, any portion of the pattern that is k equal increments long encodes one label of the ordered sequence;
obtaining, for at least a first pixel in the first imaging detector, along at least one line that is parallel to the movement direction, a first sequence of k signal values indicative of the k binary elements of a first label from the ordered sequence of labels; and
correlating, by a processor, the at least the first pixel in the first imaging detector to the surface.

2. The method of claim 1 further comprising:
obtaining, for at least a second pixel in a second imaging detector, along the at least one line that is parallel to the movement direction, the first sequence of k signal values indicative of the k binary elements of the first label from the ordered sequence of labels; and
correlating the at least the second pixel in the second imaging detector to the at least the first pixel in the first imaging detector.

3. The method of claim 1 wherein the pattern is a binary pattern.

4. The method of claim 1 wherein the ordered sequence of labels is part of a de Bruijn cycle.

5. The method of claim 1 wherein projecting the sequence of k images comprises directing lines of light in the blue spectrum.

6. A method for registering first and second imaging detectors to a surface, the method comprising:
projecting a sequence of k images toward the surface, wherein k≥4, and wherein each of the k images comprises a pattern comprising a plurality of lines of light that extend in a direction that is orthogonal to a movement direction, wherein the transition from each one of the k images to the next image in the sequence is achieved by a spatial shift of the pattern by an equal increment along the movement direction so that the leftmost image is removed and the next image in the sequence is appended as a right-most image in the pattern, and wherein the pattern encodes an ordered sequence of labels, each label having k binary elements, such that, in the movement direction, any portion of the pattern that is k equal increments long encodes one label of the ordered sequence;
obtaining, for at least a first pixel in the first imaging detector and at least a second pixel in the second imaging detector, along at least one line that is parallel to the movement direction, a first sequence of k signal values indicative of the k binary elements of a first label from the ordered sequence of labels; and
correlating, by a processor, the first and second imaging detectors to each other according to the obtained first sequence of k signal values.

7. The method of claim 6 wherein the pattern is a binary pattern.

8. The method of claim 6 wherein the ordered sequence of labels is part of a de Bruijn cycle.

9. The method of claim 6 wherein directing the sequence of k images comprises projecting lines of light in the blue spectrum.

10. The method of claim 6 wherein projecting the sequence of k images comprises directing lines of light from a laser.

11. The method of claim 6 wherein the increment corresponds to one pixel in each of the imaging detectors.

12. The method of claim 6 further comprising obtaining, for at least an additional pixel along the at least one line that is parallel to the movement direction, a second sequence of k signal values indicative of the k binary elements of a second label from the ordered sequence of labels, wherein the second label is next in sequence from the first label.

13. A method for correlating an imaging detector to a surface being imaged, the imaging detector having at least one pixel, the method comprising:
projecting a sequence of k images toward the surface, wherein k≥4, and wherein each of the k images comprises a pattern comprising a plurality of lines of light that extend in a direction that is orthogonal to a movement direction, wherein the transition from each one of the k images to the next image in the sequence is achieved by a spatial shift of the pattern by an equal increment along the movement direction;

obtaining, for the at least one pixel of the imaging detector, a set of k signal values for each projected k image, along at least one line that is parallel to the movement direction;

using the set of k signal values, assigning a label to the at least one pixel;

using the set of k signal values, assigning a first cost metric to the label of the at least one pixel;

assigning a second cost metric to the label of at least one pixel based on the label ordering sequence; and adjusting the pixel labels to reduce the first and second cost metrics.

14. The method of claim 13 wherein assigning the second cost metric is based on the label ordering sequence as determined by the deBruijn subcycle.

15. The method of claim 13 wherein the assigning the second cost metric is based on labels of prior and subsequent pixels.

* * * * *